(12) United States Patent
Jacobs et al.

(10) Patent No.: US 8,752,701 B2
(45) Date of Patent: Jun. 17, 2014

(54) PACKAGING SYSTEM FOR BRACHYTHERAPY DEVICES

(75) Inventors: Charles Jacobs, Loganville, GA (US); Russell Riescher, Loganville, GA (US); Christopher D. Drobnik, Wauconda, IL (US)

(73) Assignee: C. R. Bard, Inc., Murray Hill, NJ (US)

( * ) Notice: Subject to any disclaimer, the term of this patent is extended or adjusted under 35 U.S.C. 154(b) by 159 days.

(21) Appl. No.: 12/089,193

(22) PCT Filed: Oct. 11, 2006

(86) PCT No.: PCT/US2006/039621
§ 371 (c)(1),
(2), (4) Date: Apr. 3, 2008

(87) PCT Pub. No.: WO2007/047280
PCT Pub. Date: Apr. 26, 2007

(65) Prior Publication Data
US 2009/0223851 A1     Sep. 10, 2009

Related U.S. Application Data

(60) Provisional application No. 60/725,956, filed on Oct. 12, 2005, provisional application No. 60/744,759, filed on Apr. 13, 2006.

(51) Int. Cl.
*B65B 5/06*     (2006.01)
(52) U.S. Cl.
USPC ........... 206/438; 206/564; 206/563; 206/570; 206/370; 250/505.1
(58) Field of Classification Search
USPC .............. 206/570, 370, 438, 459.5, 562–565; 250/505.1
See application file for complete search history.

(56) References Cited

U.S. PATENT DOCUMENTS 3,802,555 A * 4/1974 Grasty et al. .................. 206/572
4,736,850 A    4/1988 Bowman et al.
(Continued)

FOREIGN PATENT DOCUMENTS

JP     63186636 A     8/1988
JP     06-270977 A     9/1994
(Continued)

OTHER PUBLICATIONS

EP 06825727.8 filed Apr. 21, 2008 Examination Report dated Aug. 17, 2010.

(Continued)

*Primary Examiner* — Andrew Perreault
(74) *Attorney, Agent, or Firm* — Rutan & Tucker, LLP (57) ABSTRACT

A brachytherapy packaging system is disclosed including an inner tray containing a plurality of recesses, each recess for holding a strand of linked radiological seeds separated by spacers. An inner tray cover may also contain a plurality of recesses that coincide with the recesses of the inner tray when placed over the inner tray. The inner tray and inner tray cover may be supported by and enclosed in a container made out of a metal such as pewter. A retainer may also be supportable on the top of the container, shaped for holding a forceps or tweezers. An outer tray may be used for supporting and enclosing the container and optional retainer. The outer tray may be sealed with a removable sheet adhesively attached to a rim of the outer tray. Different configurations of the inner tray and inner tray cover may be used for different packaging configurations.

17 Claims, 9 Drawing Sheets

(56) References Cited

U.S. PATENT DOCUMENTS

| | | | |
|---|---|---|---|
| 5,199,567 A * | 4/1993 | Discko, Jr. | 206/563 |
| 5,460,592 A | 10/1995 | Langton et al. | |
| 5,538,134 A | 7/1996 | Pitesky | |
| 5,827,995 A * | 10/1998 | Graham | 102/307 |
| 6,010,446 A | 1/2000 | Grimm | |
| 6,132,358 A * | 10/2000 | Glenn et al. | 600/3 |
| 6,830,149 B2 * | 12/2004 | Merboth et al. | 206/438 |
| 6,969,344 B2 | 11/2005 | Drobnik et al. | |
| 7,100,771 B2 * | 9/2006 | Massengale et al. | 206/570 |
| 7,190,895 B1 | 3/2007 | Groves et al. | |
| 2002/0185406 A1 * | 12/2002 | Massengale et al. | 206/571 |
| 2004/0158117 A1 | 8/2004 | Drobnik et al. | |
| 2005/0191207 A1 * | 9/2005 | Terwilliger et al. | 422/28 |
| 2005/0205445 A1 * | 9/2005 | Seiler et al. | 206/363 |

FOREIGN PATENT DOCUMENTS

| | | | |
|---|---|---|---|
| WO | 2004026111 | A2 | 4/2004 |
| WO | 2005051457 | A2 | 6/2005 |

OTHER PUBLICATIONS

EP 06825727.8 filed Apr. 21, 2008 Examination Report dated Jan. 27, 2010.
EP 06825727.8 filed Apr. 21, 2008 Examination Report dated Jun. 18, 2010.
EP 06825727.8 filed Apr. 21, 2008 Extended European Search Report dated Sep. 23, 2009.
PCT/US2006/039621 filed Oct. 11, 2006 International Preliminary Report on Patentability dated Apr. 16, 2008.
PCT/US2006/039621 filed Oct. 11, 2006 International Search Report dated Apr. 4, 2007.
PCT/US2006/039621 filed Oct. 11, 2006 Written Opinion dated Apr. 4, 2007.
AU 2006304089 filed Apr. 3, 2008 Examiners Report dated Aug. 15, 2011.
JP 2008-535630 filed Apr. 11, 2006 Office Action dated Oct. 25, 2011.
EP 06825727.8 filed Apr. 21, 2008 Examination Report dated Feb. 20, 2012.
EP 06825727.8 filed Apr. 21, 2008 Notice of Abandonment dated Aug. 3, 2012.
JP 2008-535630 filed Apr. 11, 2006 Office Action dated Feb. 2, 2012.
CA 2,624,952 filed Oct. 11, 2006 Examiners Report dated Nov. 13, 2012.
JP 2008-535630 filed Apr. 11, 2006 Notice of Allowance dated Feb. 15, 2013.

* cited by examiner

PACKAGING SYSTEM FOR BRACHYTHERAPY DEVICES

This application is a U.S. national stage application under 35 USC §371 of International Patent Application No. PCT/US2006/039621, filed Oct. 11, 2006, which claims priority to U.S. Provisional Patent Application No. 60/725,956, filed Oct. 12, 2005, and U.S. Provisional Patent Application No. 60/744,759, filed Apr. 13, 2006, each of which is incorporated by reference into this application as if fully set forth herein.

BACKGROUND OF THE INVENTION

Victims of cancer are often treated using chemotherapy and/or radiation therapy. Chemotherapy is the treatment of cancer using drugs that destroy cancer cells. Radiation therapy is the use of a type of energy, called ionizing radiation, to destroy cancer cells.

Brachytherapy is one type of radiation therapy used to treat cancer. Brachytherapy involves placing a small amount of radioactive material inside the body, near the cancer cells or tumor. Unlike external radiation treatment such as electron beam irradiation, brachytherapy enables a doctor to use a higher total dose of radiation to treat a small area in a shorter amount of time. Brachytherapy may be temporary or permanent. In temporary brachytherapy, radioactive material is placed near the cancer cells or tumor for a fixed period of time, and then withdrawn. In permanent brachytherapy, radioactive material in the form of "seeds" is permanently placed near the cancer cells or tumor. Although the seeds remain in the body permanently, the radiation levels of the seeds drop off over time.

Brachytherapy has been used in the treatment of numerous types of cancer, including cervical, breast, lung, head and neck, and prostate. For example, prostate cancer may be treated using Palladium-103 or Iodine-125 seeds. Depending on the prostate size and aggressiveness of the cancer, a health care provider can determine the number and positioning of the radioactive seeds needed to deliver a sufficient amount of radiation to kill the cancerous cells. In certain brachytherapy delivery systems, the requisite number of radioactive seeds, separated by bio-absorbable spacers, were loaded into brachytherapy needles and inserted into the prostate. Once the tip of the needle has been placed in its proper position, the needle is withdrawn, leaving a pattern of seeds and/or spacers.

Proper seed placement and seed retention at the implantation site influence the success or failure of a brachytherapy procedure. Certain seed implantation devices and methods often provide variable seed spacing and dosimetric patterns during and after implantation. Loose seeds, especially those that are extra-capsular (located outside the capsule of the prostate), tend to migrate within the patient, and as a result, may not provide radiation where needed and may sometimes cause damage to other radiation-sensitive areas of the body. In addition, the manual loading of seeds and connectors and/or spacers into the brachytherapy needle can be a laborious and time-consuming task.

As a result of the above, "stranded" seeds have been developed. Stranded seeds are connected together by connective material to form a strand. The seeds in a particular strand may be spaced apart by a predetermined interval to create a desired dosing level. By varying the spacing of seeds and the lengths of strands, strands can be formed with different desired dosing levels.

To facilitate the formation of strands of seeds, a brachytherapy seed deployment system has been disclosed in U.S. Pat. No. 6,010,446; and U.S. Pat. No. 6,969,344 (the contents of each of which are incorporated by reference as if fully set forth herein). The system comprises a basic unit of at least two seeds and a connector joining the seeds to maintain proper spacing between the seeds. Further alternating connectors and seeds may be connected to this basic unit to form a strand of seeds, each seed separated from adjacent seeds by the length of the connectors. The length of the connectors and the overall length of the strand may be varied to create a desired dosing level depending on patient needs. The connectors may be formed of solid rods of bioabsorbable material that degrade within 18-24 months after being inserted into the body. Suitable connectors include the SourceLink™ connectors sold by Bard Brachytherapy.

Figure 1:
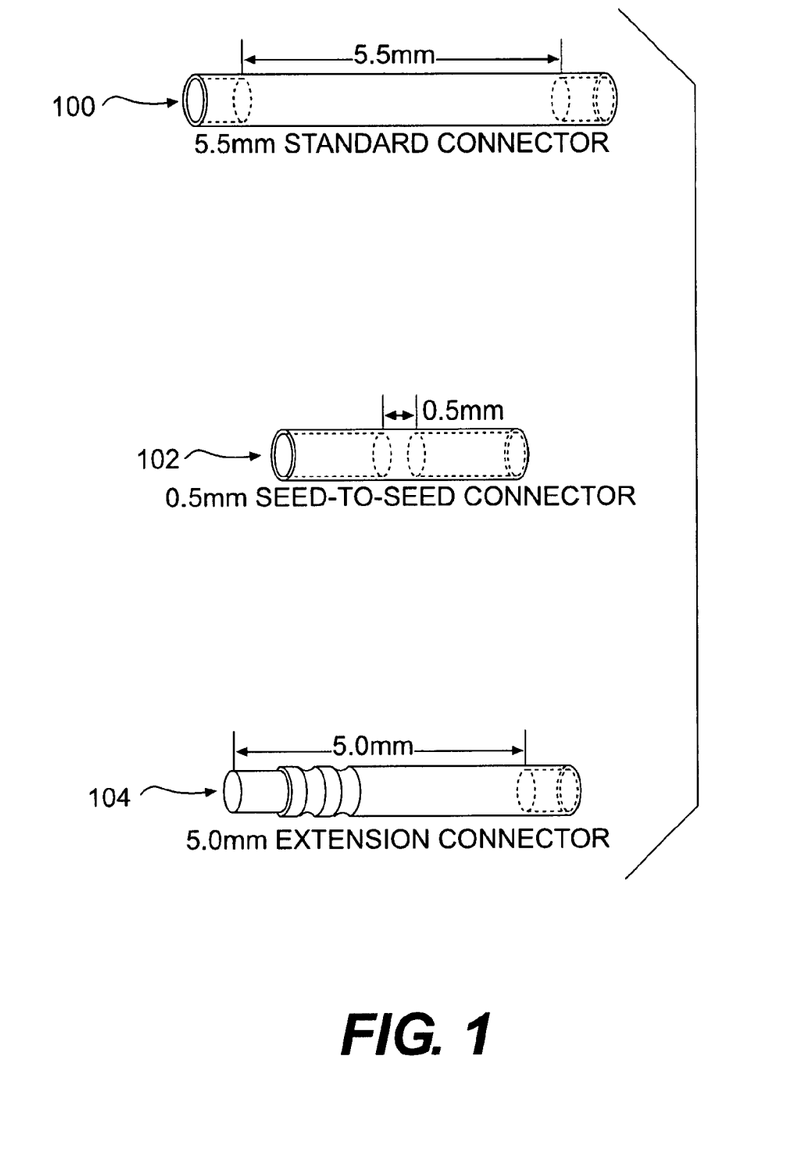
FIG. 1 illustrates three components of an exemplary brachytherapy seed deployment system designed to provide seed spacing in 0.5 cm increments.

FIG. 1 illustrates three components of an exemplary brachytherapy seed deployment system designed to provide seed spacing in 0.5 cm increments. Reference character 100 designates an exemplary 5.5 mm standard connector, reference character 102 designates an exemplary 0.5 mm seed-to-seed connector, and reference character 104 designates an exemplary 5.0 mm extension connector. Used together, these components may form strands of certain lengths with certain seed spacings.

To apply these strands to the cancer cells or tumor, a hollow tube delivery device such as a needle, catheter or applicator may first be inserted into the affected area. Strands are then placed in the delivery device and either pushed into the proper location, or the delivery device is drawn out and the strands are seated in the proper location. Alternatively, the strands may first be placed into the delivery device prior to the insertion of the delivery device into the body. X-rays, ultrasound or CT scans may be among the tools used to ensure that the seeds in the strands are properly placed.

In temporary brachytherapy, the strands and the delivery device are inserted into the affected area and later removed from the body. In High-Dose Rate (HDR) brachytherapy, a specific high dose of radiation is delivered to the affected area through the delivery device for a short period of time controlled by a computer. This process may be repeated several times over the course of a single day. In Low-Dose Rate (LDR) brachytherapy, a lower dose of radiation is continuously delivered to the affected area through the delivery device over the course of hours or days.

In permanent brachytherapy, the strands may be left in the body after the delivery device is removed. The radioactivity of the seeds decays over time, and thereafter pose no threat to healthy tissues.

Cancer patients in need of brachytherapy may require certain treatment regimes, i.e. particular dosing levels that call for a discrete number of radiological seeds spaced apart by a predetermined distance in a strand of a particular length. For example, different dosing levels may be required depending on, e.g., the size of the patient, the nature of the tissue in which the seeds are to be implanted, and the type of cancer being treated. However, in conventional brachytherapy packaging services, little flexibility is provided, especially when on-site loading of strands is preferred by the health care provider. Conventional brachytherapy packaging services for on-site loading provide standard arrays of seeds to the health care provider regardless of the needs of the patient.

Thus, there is a need for a brachytherapy packaging system that is capable of delivering a particular number of strands of various lengths and predetermined seed spacings as requested by the health care provider. Such a packaging system would enable the health care provider to perform on-site loading and verification of dosing while avoid the expense of providing unnecessary and/or excessive quantities of strand configurations.

BRIEF SUMMARY

Accordingly, a brachytherapy packaging system and brachytherapy kit is described herein, the brachytherapy kit in one embodiment including at least one inner tray containing a plurality of recesses, each of which is configured to hold a strand of linked radiological seeds separated by connectors. The kit may also include an inner tray cover that may also contain a plurality of recesses that coincide with (are aligned with) the recesses of the inner tray when placed over the inner tray to retain the strands in the recesses. The inner tray and/or inner tray cover may be made out of a plastic such as polyethylene terephthalate (PET) or other suitable material.

The inner tray and inner tray cover may be supported by and enclosed in a container. The container may be made out of a metal such as pewter that offers some shielding from the radioactive seeds contained therein, and may be formed as two separate pieces, two pieces connected in a clamshell configuration, or any other configuration capable of supporting and enclosing the inner tray and inner tray cover, and capable of providing shielding for the strands retained within the inner tray and inner tray cover.

A retainer may also be supportable on the top of the container, and be shaped for holding various objects, such as medical instruments, for example forceps or tweezers. An outer tray may be used for supporting and enclosing the container and optional retainer. The outer tray may be sealed with a cover, which may comprise a removable sheet adhesively attached to a rim of the outer tray. The retainer, outer tray and outer tray cover may be made out of a plastic such as PET or other suitable material.

The brachytherapy packaging system includes different configurations of the inner tray and inner tray cover to allow for different packaging configurations. This allows for the health care provider to request a precise number of strand configurations sufficient for a given patient, and receive the precise number of strand configurations in the inner tray configuration best suited for maintaining the structure of the pre-connected seed and connector strands and retaining the strand configurations during shipping. The brachytherapy kit supports dynamic dosimetry and enables a health care provider to perform on-site needle loading and obtain visual confirmation of load configurations, while providing flexibility to accommodate the health care provider's technique-related and logistics-related needs. The strands may also be broken on-site to shorten the length of the strands.

One exemplary inner tray configuration may include recesses for retaining up to 15 strands of no greater than a first fixed length, recesses for retaining up to eight strands of no greater than a second fixed length, and one recess for retaining one strand of no greater than a third fixed length. Another exemplary inner tray configuration may includes recesses for retaining up to 15 strands of no greater than a fourth fixed length, recesses for retaining up to 15 strands of no greater than a fifth fixed length, recesses for retaining up to 15 strands of no greater than a sixth fixed length, recesses for retaining up to four strands of no greater than the second fixed length, and one recess for retaining one strand of no greater than the third fixed length. Yet another exemplary inner tray configuration may include recesses for retaining up to 30 strands of no greater than a seventh fixed length.

Although three examples have been provided above, it should be understood that the brachytherapy kit may receive other inner tray configurations as well. For example, inner tray designs with recesses in first and second directions and indented regions at some or all of the intersections of the recesses allow a single inner tray design to be used for multiple configurations, thereby potentially saving manufacturing costs. For example, such an inner tray design may be used in a first configuration where strands may be placed only in the recesses running in the first direction, or in a second configuration where strands may be placed only in the recesses running in the second direction. In other designs, recesses may be oriented diagonally within the inner tray to enable longer strands to be retained.

These and other embodiments, methods, features and advantages will become more apparent to those skilled in the art when taken with reference to the following more detailed description of the disclosure in conjunction with the accompanying drawings that are first briefly described.

The following description should be read with reference to the drawings. The drawings, which are not necessarily to scale, depict selected embodiments and are not intended to limit the scope of the invention. The description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Embodiments of the present invention relate generally to a packaging system for brachytherapy, specifically packaging for a brachytherapy kit. It should be noted that the brachytherapy packaging system and kit, as described herein, may be used for a number of different applications, such as, but not limited to, the treatment of prostate, cervical, breast, lung, head and neck cancer and tumors.

Figure 2A:
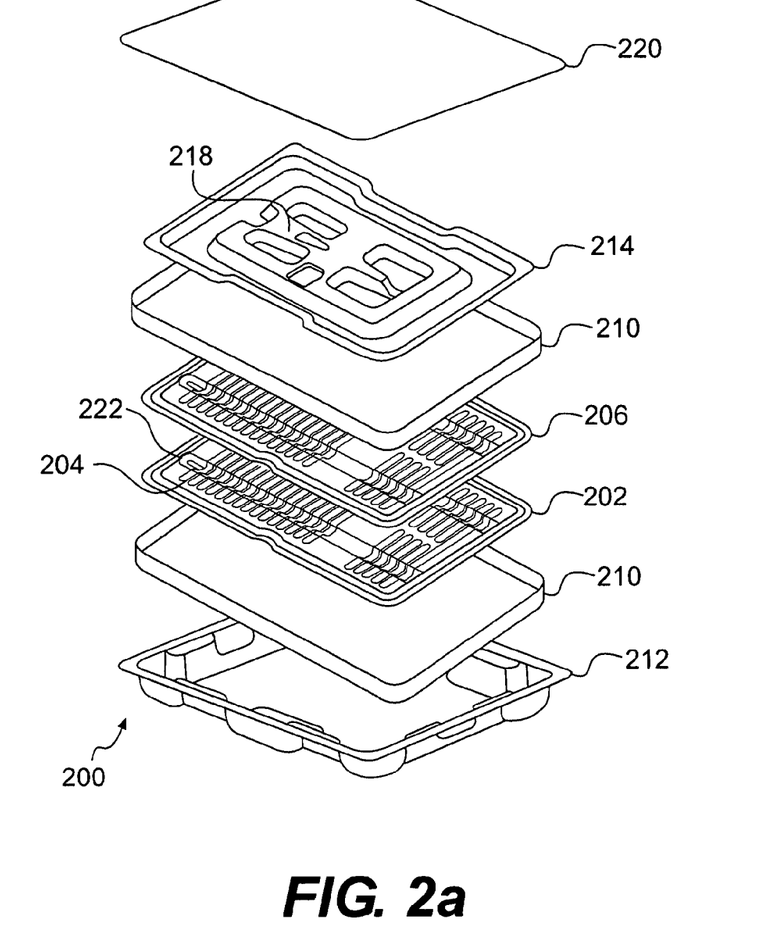
FIG. 2a is an exploded perspective view of an exemplary brachytherapy kit according to various embodiments of the present disclosure.

FIG. 2a illustrates an exploded perspective view of an exemplary brachytherapy kit 200 according to embodiments of the present invention. The brachytherapy kit 200 may include at least one inner tray 202. The inner tray 202 may contain a plurality of recesses 204, each of which is configured to hold a strand of linked radiological seeds separated by connectors. The strands may be formed from seeds and connecting spacers as shown in FIG. 1, but it should be understood that the seeds and connectors of FIG. 1 are only exemplary, and that other seed-connector configurations may be used. In one embodiment, the recesses may be shaped as troughs arranged in one or more groups, with the recesses of each group aligned in parallel with each other. The recesses may be linear or formed in any shape necessary to conform to the strands to be held, and the groups of recesses may be aligned in one or more directions in the inner tray 202.

The inner tray 202 may also contain indented regions 222, which provide an area at which the strands can be grasped by a tool such as tweezers. The indented regions 222 may be oriented in a different direction as compared to the recesses 204 (e.g. perpendicular to the recesses), and may be at the same level as the recesses or deeper than the recesses. The indented regions 222 may be also be shaped as troughs, and may be wider than the recesses, or may be circular or formed in any shape that allows for removal of the strands.

The kit 200 may also include an inner tray cover 206 that may also contain a plurality of recesses 208 that coincide with (are aligned with) the recesses of the inner tray 204 when placed over the inner tray to retain the strands in the recesses. In one embodiment, the inner tray cover 206 is shaped similarly to the inner tray 202. The inner tray 202 and/or inner tray cover 206 may be made out of a plastic such as polyethylene terephthalate (PET) or other suitable material, may be clear or opaque, and may be formed as two separate pieces, two pieces connected in a clamshell configuration, or any other configuration capable of retaining the strands within.

The brachytherapy kit 200 according to embodiments of the present invention may also include a container 210 for supporting and enclosing the inner tray and inner tray cover. The container 210 may be made out of a metal such as pewter that offers some shielding from the radioactive seeds contained therein, and may be formed as two separate pieces, two pieces connected in a clamshell configuration, or any other configuration capable of supporting and enclosing the inner tray 202 and inner tray cover 206, and capable of providing shielding for the strands retained within the inner tray and inner tray cover.

The brachytherapy kit 200 according to embodiments of the present disclosure may also include an outer tray 212 for holding the container. A retainer tray 214 may also be supportable on the top of the container 210 within the outer tray 212, and be shaped for holding a forceps or tweezers in recess 218. The kit 200 may also include an outer tray cover 220, which may comprise a removable sheet adhesively attached to a rim of the outer tray 212, a separate cover formed separately from the outer tray or connected to the outer tray in a clamshell configuration, or any other configuration for supporting and enclosing the container and optional retainer within in a sterile manner. The retainer tray 214 and outer tray 212 may be made out of a plastic such as PET or other suitable material, and may be clear or opaque. All packaging material in the brachytherapy kit 200 may be disposable.

Figure 2B:
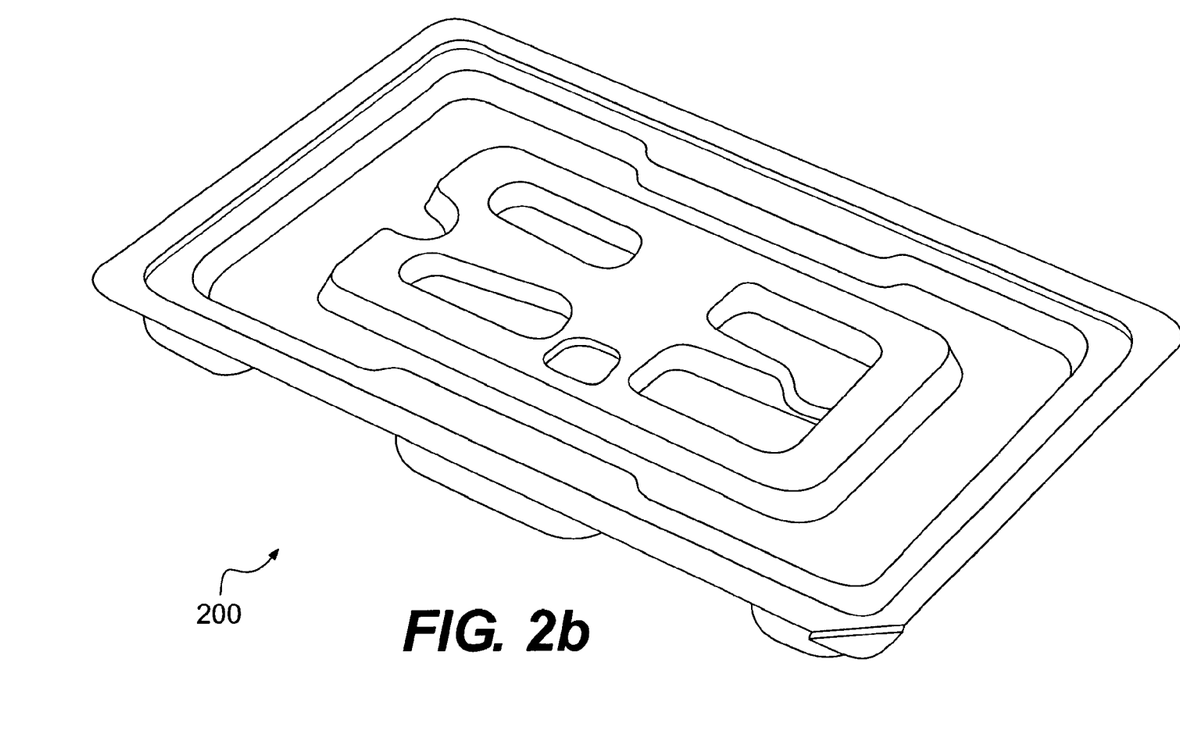
FIG. 2b is a perspective view of an exemplary assembled brachytherapy kit of the type illustrated in FIG. 2a with the outer tray cover removed according to various embodiments of the present disclosure.

FIG. 2b is a perspective view of an exemplary assembled brachytherapy kit 200 of the type illustrated in FIG. 2a, with the outer tray cover 220 removed, according to embodiments of the present disclosure. The packaging of the brachytherapy kit 200 may be disposable.

In the brachytherapy packaging system according to embodiments of the present invention, different configurations of the inner tray and inner tray cover may be available to allow for different packaging configurations. The different configurations hold different strand configuration types and quantities that correlate to different types of expected orders from health care providers.

Figure 3A:
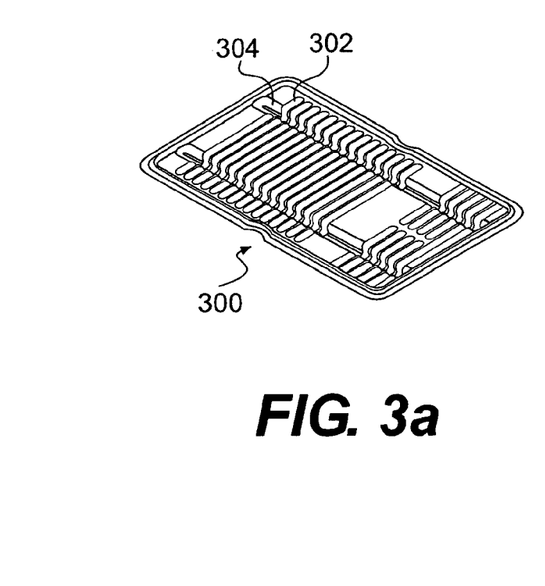
FIG. 3a illustrates a perspective view of one exemplary inner tray configuration loaded with strands according to various embodiments of the present disclosure.

FIG. 3a illustrates a perspective view of one exemplary standard inner tray configuration 300 loaded with strands according to embodiments of the present invention. In the example of FIG. 3a, inner tray configuration 300 includes recesses 302 shaped and sized for retaining the strands, and indented regions 304 shaped and sized for allowing easy access to the strands using a tool such as a forceps or tweezers.

Figure 3B:
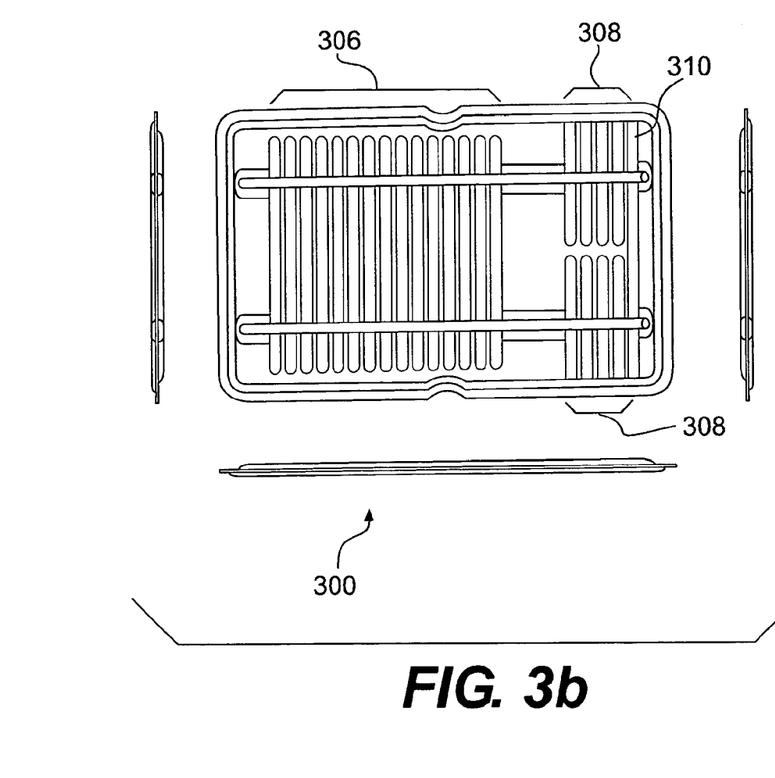
FIG. 3b illustrates an orthographic view of the exemplary inner tray configuration of FIG. 3a according to various embodiments of the present disclosure.

FIG. 3b illustrates an orthographic view of the exemplary inner tray configuration 300 of FIG. 3a according to embodiments of the present disclosure. Inner tray configuration 300 includes recesses 306 for retaining up to 15 strands of no greater than a particular length (e.g. 15 pre-connected trains of 10 seeds and connectors with 1.0 cm seed-to-seed spacing), recesses 308 for retaining up to eight strands of no greater than another particular length (e.g. eight custom trains of seeds and connectors no longer than 5.0 cm in length), and one recess 310 for retaining one strand of no greater than yet another particular length (e.g. one custom train no longer than 10.0 cm in length). Note that in embodiments of the present disclosure, markings on the inner tray near the recesses may be provided to indicate information about the strands retained in those recesses, such as, for example, the strand configuration type.

Figure 4A:
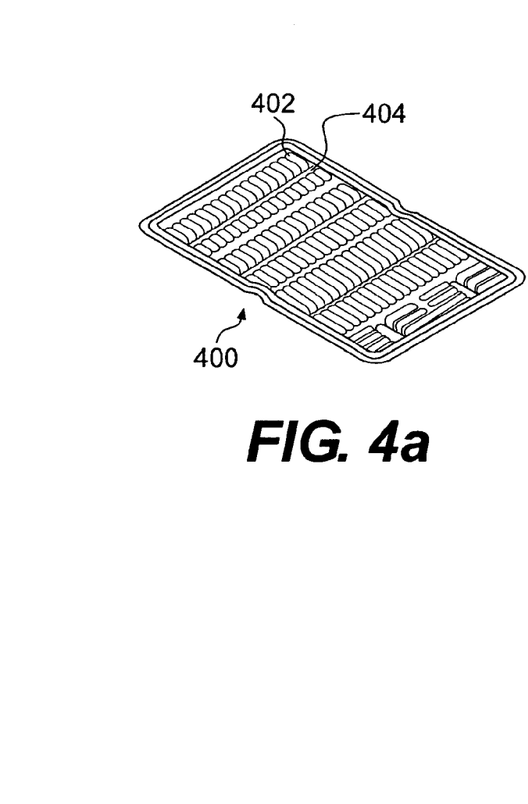
FIG. 4a illustrates a perspective view of another exemplary inner tray configuration loaded with strands according to various embodiments of the present disclosure.

FIG. 4a illustrates a perspective view of another exemplary variable inner tray configuration 400 loaded with strands according to embodiments of the present disclosure. In the example of FIG. 4a, inner tray configuration 400 includes recesses 402 for retaining the strands, and indented regions 404 for allowing easy access to the strands.

Figure 4B:
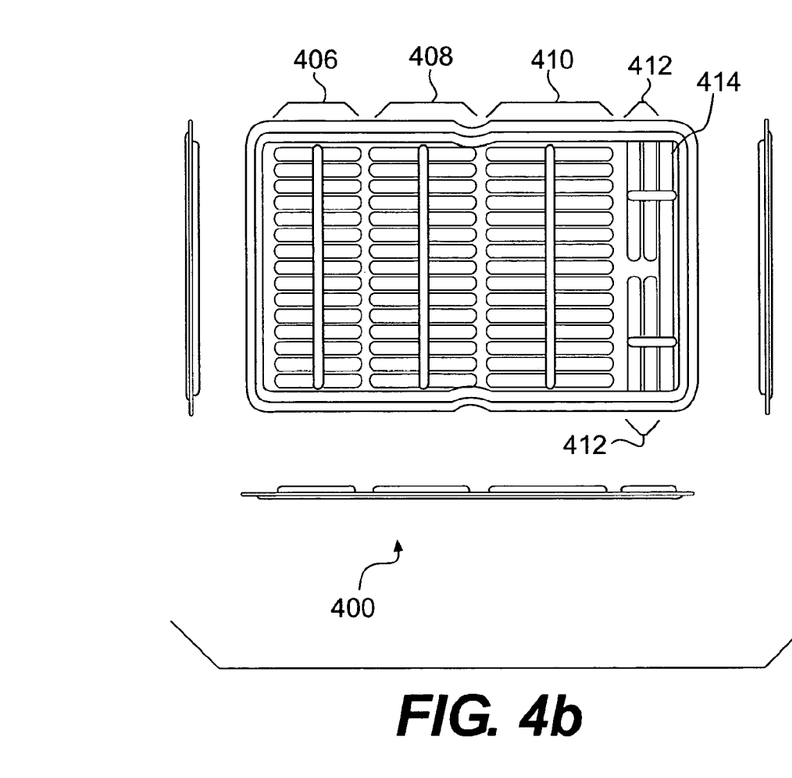
FIG. 4b illustrates an orthographic view of the exemplary inner tray configuration of FIG. 4a according to various embodiments of the present disclosure.

FIG. 4b illustrates an orthographic view of the exemplary inner tray configuration 400 of FIG. 4a according to embodiments of the present invention. Inner tray configuration 400 includes recesses 406 for retaining up to 15 strands of no greater than a particular length (e.g. 15 pre-connected trains of three seeds and connectors with 1.0 cm seed-to-seed spacing), recesses 408 for retaining up to 15 strands of no greater than another particular length (e.g. 15 pre-connected trains of four seeds and connectors with 1.0 cm seed-to-seed spacing), recesses 410 for retaining up to 15 strands of no greater than yet another particular length (e.g. 15 pre-connected trains of five seeds and connectors with 1.0 cm seed-to-seed spacing), recesses 412 for retaining up to four strands of no greater than still another particular length (e.g. four custom trains of seeds and connectors no longer than 5.0 cm in length), and one recess 414 for retaining one strand of no greater than one other particular length (e.g. one custom train no longer than 10.0 cm in length). Note that in embodiments of the present disclosure, markings on the inner tray near the recesses may be provided to indicate information about the strands retained in those recesses, such as, for example, the number of seeds in the strands or the strand configuration type.

Figures 5A, 5B:
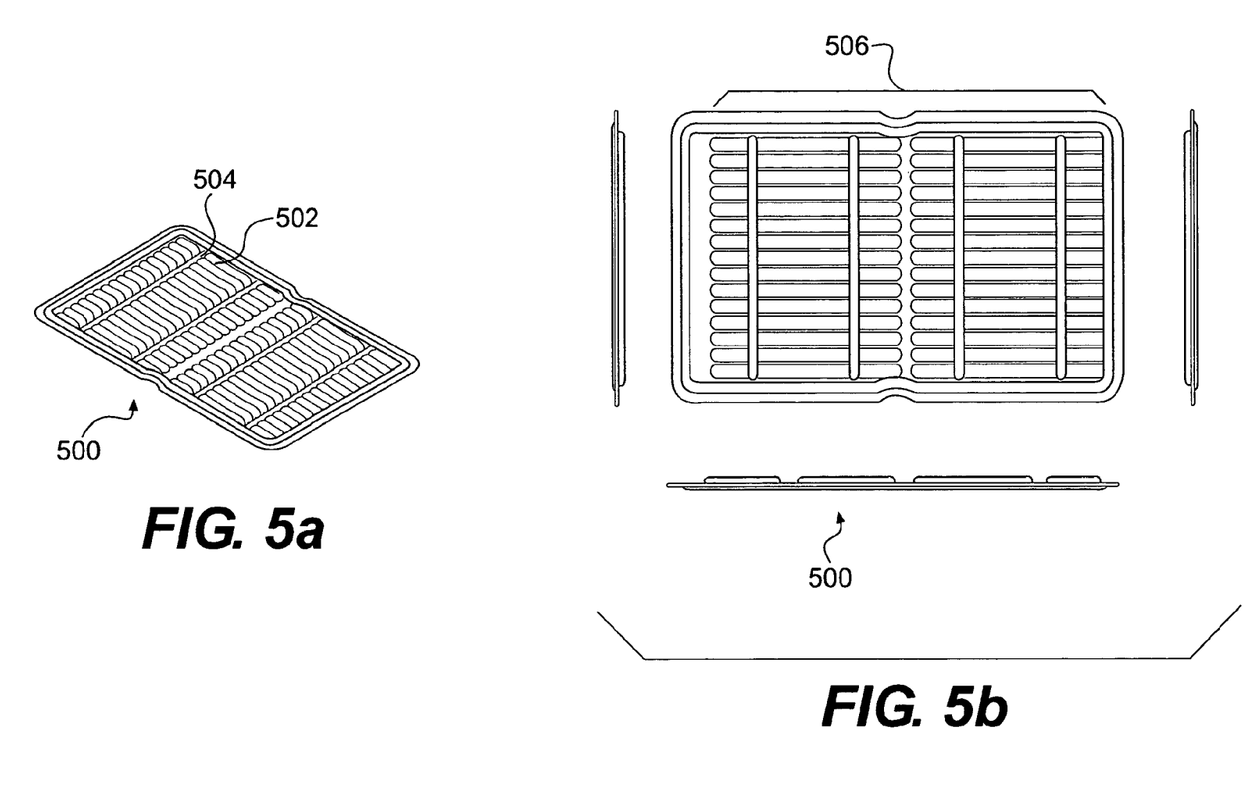
FIG. 5a illustrates a perspective view of yet another exemplary inner tray configuration loaded with strands according to various embodiments of the present disclosure.
FIG. 5b illustrates an orthographic view of the exemplary inner tray configuration of FIG. 5a according to various embodiments of the present disclosure.

FIG. 5a illustrates a perspective view of yet another exemplary prescription inner tray configuration 500 loaded with strands according to embodiments of the present invention. In the example of FIG. 5a, inner tray configuration 500 includes recesses 502 for retaining the strands, and indented regions 504 for allowing easy access to the strands.

FIG. 5b illustrates an orthographic view of the exemplary inner tray configuration 500 of FIG. 5a according to embodiments of the present disclosure. Inner tray configuration 500 includes recesses 506 for retaining up to 30 strands of no greater than a particular length (e.g. 30 pre-connected trains of seeds and connectors no longer than 8.0 cm in length). Note that in embodiments of the present disclosure, markings on the inner tray near the recesses may be provided to indicate information about the strands retained in those recesses, such as, for example, the strand number.

Figure 6A:
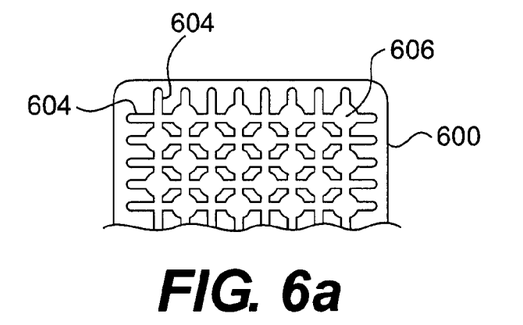
FIGS. 6a and 6b illustrate top views of portions of exemplary inner tray designs with recesses in first and second directions and indented regions at some or all of the intersections of the recesses according to various embodiments of the present disclosure.
Figure 6B:
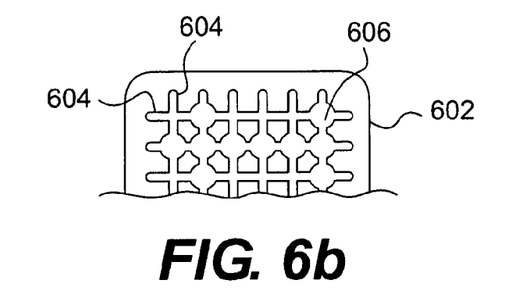
Figure 7:
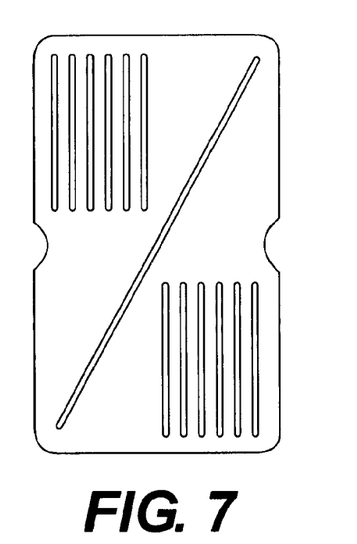
FIG. 7 illustrates a top view of an exemplary inner tray design with a diagonal recess according to various embodiments of the present disclosure.

Although three examples have been provided above in FIGS. 3a, 3b, 4a, 4b, 5a and 5b, it should be understood that the brachytherapy kit according to embodiments of the present disclosure may receive other inner tray configurations as well. For example, FIG. 6a and 6b illustrate top view portions of exemplary inner tray designs 600 and 602 with recesses 604 in first and second directions and indented regions 606 at some or all of the intersections of the recesses according to embodiments of the present invention. With these designs, a single inner tray design can be used for multiple configurations, thereby potentially saving manufacturing costs. For example, the single inner tray design of FIGS. 6a and 6b may be used in a first configuration where strands may be placed only in the recesses running in the first direction. Alternatively, the same inner tray design may be used in a second configuration where strands may be placed only in the recesses running in the second direction. In other embodiments, no indented regions may be needed, as the empty recesses perpendicular to the recesses holding strands may be used to enable removal of the strands. In a further exemplary embodiment illustrated in FIG. 7, one or more recesses may be oriented diagonally within the inner tray to enable longer strands to be retained. One skilled in the art will recognize that other configurations are possible, depending on the strand configuration types to be retained, and that these other configurations fall within the scope of the present disclosure.

Figure 8A:
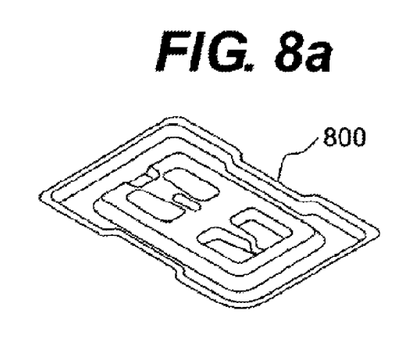
FIGS. 8a, 8b and 8c are perspective, orthographic and bottom views, respectively, of an exemplary retainer that may be supportable on the top of the container within the outer tray of FIG. 2, and be shaped for retaining a forceps according to various embodiments of the present disclosure.
Figure 8B:
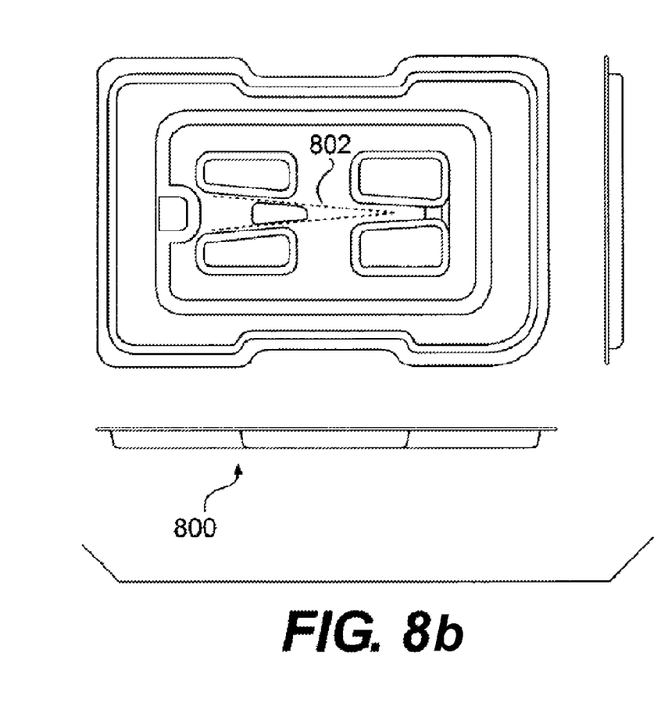
Figure 8C:
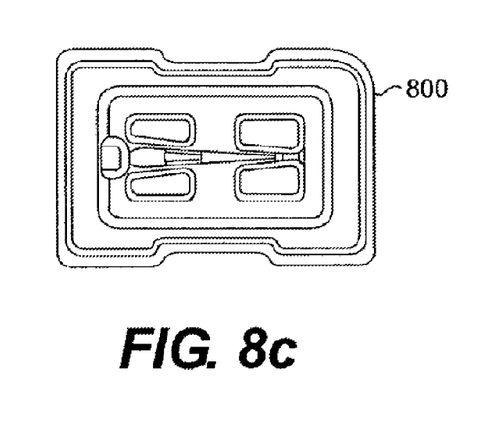

FIGS. 8a, 8b and 8c are perspective, orthographic and bottom views, respectively, of an exemplary retainer tray 800 that may be supportable on the top of the container 210 within the outer tray 212 of FIG. 2, and be shaped for retaining a forceps 802, illustrated in dashed outline in FIG. 8b, according to embodiments of the present disclosure. It should be understood, however, that many other retainer configurations could be employed and fall within the scope of the present disclosure.

Figure 9A:
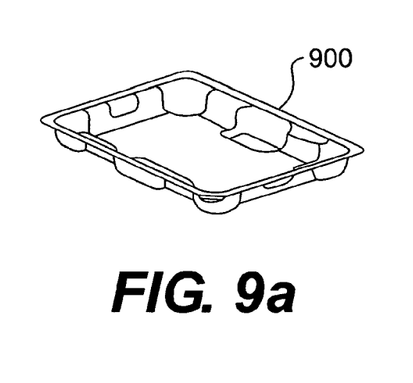
FIGS. 9a and 9b are perspective and orthographic views, respectively, of an exemplary outer tray for supporting and enclosing the container and optionally the retainer of FIG. 2 according to various embodiments of the present disclosure.
Figure 9B:
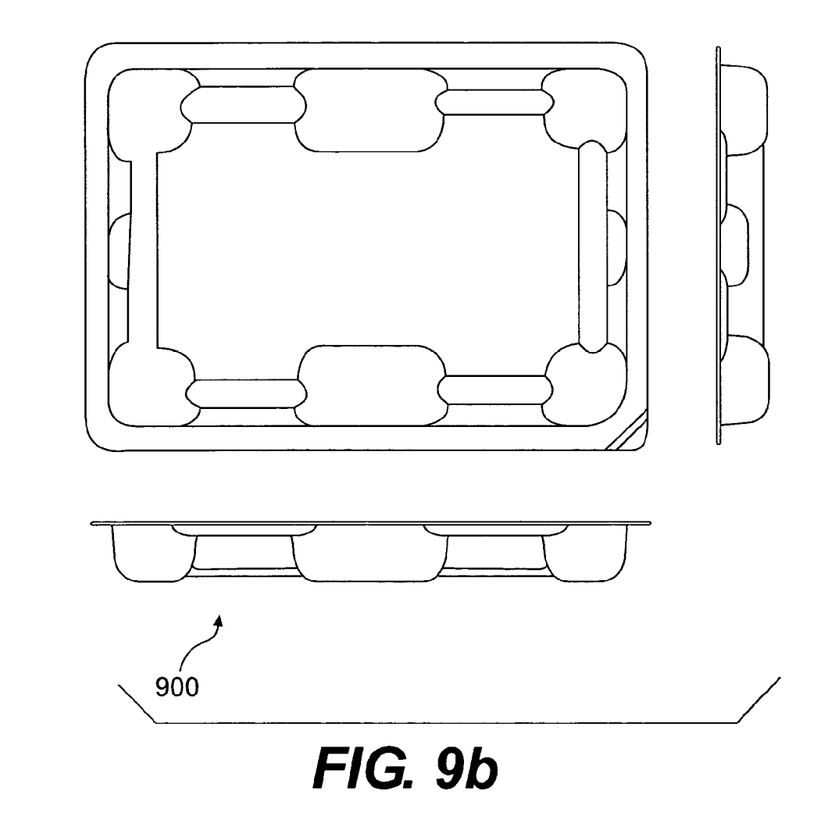

FIGS. 9a and 9b are perspective and orthographic views, respectively, of an exemplary outer tray 900 for supporting and enclosing the container 210 and optionally the retainer tray 214 of FIG. 2 according to embodiments of the present disclosure. It should be understood, however, that many other retainer configurations could be employed and fall within the scope of the present disclosure.

To utilize the brachytherapy packaging system according to embodiments of the present disclosure, a health care provider may first request the strand configurations and quantities needed for a given patient. Upon receiving the order, the requested strands are assembled from seeds and connectors, and are placed in the inner tray configuration best suited for maintaining the structure of the pre-connected seed and connector strands and retaining the strand configurations during shipping. After the inner tray is populated with the requested strands, the remainder of the brachytherapy kit, including the inner tray cover, container, retainer, outer tray, and outer tray cover may be assembled in a sterile manner and shipped to the health care provider. The health care provider then receives the brachytherapy kit containing the precise number of strand configurations and quantities requested, which results in the elimination of excess quantities and expense.

As described and illustrated above, the brachytherapy kit sets out the strands in an organized, non-overlapping manner, in recesses that may be labeled to facilitate easy identification by the health care provider. The brachytherapy kit thus supports dynamic dosimetry and enables a health care provider to perform on-site needle loading and obtain visual confirmation of load configurations, while providing flexibility to accommodate the health care provider's technique-related and logistics-related needs. The strands may also be intentionally broken on-site by the health care provider to shorten the length of the strands.

In other embodiments of the present disclosure, pursuant to the health care provider's request, extra calibrated seeds, connectors or spacers may also be provided in separate vials or in unused recesses in the inner tray.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A packaging system for pre-connected strands of brachytherapy seeds separated by connectors, the system comprising:
   a plurality of pre-connected strands of brachytherapy seeds separated by connectors, wherein the plurality of pre-connected strands is customized for a particular patient;
   an inner tray including an inner tray configuration having a plurality of recesses, wherein:
   each individual recess conforms to a pre-connected strand,
   multiple recesses conform to multiple different strand configurations in a non-overlapping and organized manner, and
   the inner tray configuration includes at least a first individual recess no greater than a first length and a second individual recess no greater than a second length, the first length being greater than the second length;

wherein the inner tray configuration holds the plurality of pre-connected strands in a manner that permits visual confirmation of load configurations while the plurality of pre-connected strands are held in the inner tray configuration and also permits direct access to the plurality of pre-connected strands for on-site loading.

2. The packaging system according to claim 1, wherein the inner tray configuration is a standard configuration holding a first number of strands of a first strand configuration no greater than the first length, a second number of strands of a second strand configuration no greater than the second length, and a third number of strands of a third strand configuration no greater than a third length, wherein the second length is greater than the third length.

3. The packaging system according to claim 1, wherein the inner tray configuration is a variable configuration holding a first number of strands of a first strand configuration no greater than the first length, the first number of strands of a second strand configuration no greater than the second length, the first number of strands of a third strand configuration no greater than the third length, a second number of strands of a fourth strand configuration no greater than a fourth length, and a third number of strands of a fifth strand configuration no greater than a fifth length, wherein the second length is greater than the third length, the third length is greater than the fourth length, and the fourth length is greater than the fifth length.

4. The packaging system according to claim 1, wherein the inner tray configuration is a prescription configuration holding a first number of strands of a first strand configuration no greater than the first length.

5. The packaging system according to claim 1, wherein the inner tray configuration includes one or more indented regions enabling removal of the strands.

6. The packaging system according to claim 1, wherein the inner tray configuration includes recesses aligned in at least a first direction and a second direction, the first direction being different from the second direction.

7. The packaging system according to claim 1, further comprising an inner tray cover including an inner tray cover configuration having a plurality of recesses coincident with the plurality of recesses in the inner tray configuration when the inner tray cover is placed on top of the inner tray for retaining the plurality of pre-connected strands of brachytherapy seeds and connectors.

8. The packaging system according to claim 1, further comprising a container enclosing the inner tray.

9. The packaging system according to claim 8, wherein the container provides radiation shielding.

10. The packaging system according to claim 8, wherein the container is made of pewter.

11. The packaging system according to claim 1, further comprising a retainer tray different from the inner tray, the retainer tray including a recess shaped for retaining tweezers or forceps, the recess having at least two walls at an acute angle to each other.

12. The packaging system according to claim 8, further comprising an outer tray for holding the container.

13. The packaging system according to claim 12, further comprising an outer tray cover for enclosing the container between the outer tray cover and the outer tray in a sterile manner.

14. The packaging system according to claim 1, further comprising:
an inner tray cover including an inner tray cover configuration having a plurality of recesses coincident with the plurality of recesses in the inner tray configuration when the inner tray cover is placed on top of the inner tray for retaining the plurality of pre-connected strands of brachytherapy seeds and connectors;
a container enclosing the at least one inner tray; and
an outer tray and an outer tray cover for enclosing the container in a sterile manner.

15. The packaging system according to claim 1, wherein the plurality of recesses are arranged into at least two groups, with recesses of each group having the same length and wherein the length of the recesses in at least one group is different from the length of the recesses in at least one other group.

16. The packaging system according to claim 1, wherein indicia on the inner tray configuration near the individual recesses indicates information about the pre-connected strands retained in the individual recesses.

17. The packaging system according to claim 16, wherein the indicia is a strand configuration type.

* * * * *